United States Patent [19]

Busacca

[11] Patent Number: 4,737,502
[45] Date of Patent: Apr. 12, 1988

[54] COMPOUNDS HAVING ANTIPLATELET AGGREGATION ACTIVITY, AND PHARMACEUTICAL COMPOSITIONS CONTAINING THEM

[75] Inventor: Rosario Busacca, Milan, Italy

[73] Assignee: Ellem Industria Farmaceutica S.p.A., Milan, Italy

[21] Appl. No.: 837,407

[22] Filed: Mar. 7, 1986

[30] Foreign Application Priority Data

Mar. 14, 1985 [IT] Italy .................. 19903 A/85

[51] Int. Cl.$^4$ .................. C07D 473/08; A61K 31/52
[52] U.S. Cl. .................. 514/265; 544/267; 544/268
[58] Field of Search .................. 544/268, 267, 276; 514/265

[56] References Cited

U.S. PATENT DOCUMENTS 4,275,064 6/1981 Bodor .................. 514/265

Primary Examiner—Nicholas S. Rizzo
Attorney, Agent, or Firm—Walter H. Schneider

[57] ABSTRACT

Compounds of general formula (I)

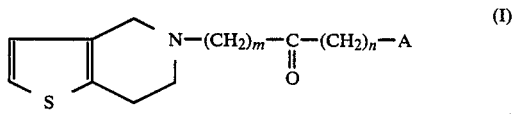

wherein:
m is zero or 1;
n is zero, 1, 2, 3 or 4;
A is a 3,7-dimethylxanthine-1-yl or 1,3-dimethylxanthine-7-yl residue;
show marked anti-platelet activity.

12 Claims, No Drawings

COMPOUNDS HAVING ANTIPLATELET AGGREGATION ACTIVITY, AND PHARMACEUTICAL COMPOSITIONS CONTAINING THEM

The present invention relates to compounds of general formula (I)

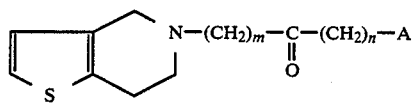

wherein:
m is zero or 1;
n is zero, 1, 2, 3 or 4;
A is a 3,7-dimethylxanthine-1-yl or 1,3-dimethylxanthine-7-yl residue;
and pharmaceutically acceptable salts thereof with inorganic or organic acids.

Preferred compounds of the invention are the following:

N-[1-keto-5-(3,7-dimethylxanthine-1-yl)pentyl]-4,5,6,7-tetrahydro-thieno[3,2-c]pyridine;
N-[2-keto-5-(3,7-dimethylxanthine-1-yl)pentyl]-4,5,6,7-tetrahydro-thieno[3,2-c]pyridine;
N-[2-keto-4-(3,7-dimethylxanthine-1-yl)butyl]-4,5,6,7-tetrahydro-thieno[3,2-c]pyridine;
N-[2-keto-3-(3,7-dimethylxanthine-1-yl)propyl]-4,5,6,7-tetrahydro-thieno[3,2-c]pyridine;
N-[2-keto-6-(1,3-dimethylxanthine-7-yl)hexyl]-4,5,6,7-tetrahydro-thieno[3,2-c]pyridine;
N-[1-keto-5-(1,3-dimethylxanthine-7-yl)pentyl]-4,5,6,7-tetrahydro-thieno[3,2-c]pyridine;
N-[2-keto-5-(1,3-dimethylxanthine-7-yl)pentyl]-4,5,6,7-tetrahydro-thieno[3,2-c]pyridine;
N-[2-keto-4-(1,3-dimethylxanthine-7-yl)butyl]-4,5,6,7-tetrahydro-thieno[3,2-c]pyridine;
N-[2-keto-3-(1,3-dimethylxanthine-7-yl)propyl]-4,5,6,7-tetrahydro-thieno[3,2-c]pyridine.

The present invention also relates to a process for the preparation of compounds (I), comprising reacting 4,5,6,7-tetrahydrothieno[3,2-c]pyridine (II) with theobromine or theophylline haloderivatives of formula (III), according to the following scheme:

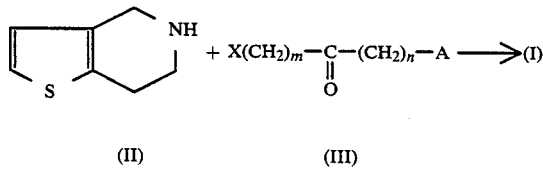

wherein m, n and A have the above mentioned meanings, whilst X represents a halogen atom, preferably chlorine or bromine. More particularly, X preferably represents chlorine when m is zero, and bromine when m=1. The reaction is preferably carried out in the presence of acid-binding agents, preferably tertiary bases such as triethylamine, pyridine and the like, in inert solvents such as acetonitrile, aromatic hydrocarbons, dimethylformamide, dimethylsulphoxide, ethers and the like; alternatively, a tertiary base excess may be used as the solvent.

The following examples illustrate the process according to the invention, without limiting it.

Melting points are not corrected; $^1$H-NMR spectra were registered by means of an EM-390 device, 90 MHz, TMS inner standard. TLC chromatograms were developed on silica gel plates Merck PF-254.

EXAMPLE 1

(a) 1-(6-Bromo-5-ketohexyl)-3,7-dimethylxanthine

50 Grams (0.18 moles) of 1-(5-keto-hexyl)-3,7-dimethylxanthine were dissolved in 490 ml of completely anhydrous methanol, at 45°–50° C. After cooling to room temperature, 32 g (0.20 moles) of bromine were added in one single portion with stirring. The solution decoloured in 1 hour. After 7 more hours of stirring, the resulting precipitate was pump filtered, the filtrate was concentrated under vacuum, yielding other precipitate which was joined to the first one, to obtain totally 33 g of dry product, consisting in the dimethylketal of the desired compound, m.p. 125°–135° C., which was hydrolyzed at room temperature, for 10 hours, in 270 ml of a dioxane/water mixture (2:1 by volume) acidified with 25–30 drops of conc. $H_2SO_4$. The mixture was left to stand overnight in the cool, the resulting precipitate was pump filtered, washed with some water, dried and crystallized from 200 ml of methanol. 28 Grams of bromoketone were obtained (43.6% of the theoric), m.p. 115°–117° C., having the following analytical characteristics:

TLC: methanol/methylene chloride 0.5/9.5: unitary spot with $R_f=0.71$; $R_f$ of the starting compound: 0.58.

$^1$H-NMR (CDCl$_3$) spectrum: 7.53δ (s, 1H, N=C$\underline{H}$); 4.01δ (superimposed signals, 5H, C$\underline{H}_3$ and C$\underline{H}_2$N); 3.93δ (s, 2H, C$\underline{H}_2$—Br); 3.60δ (s, 3H, C$\underline{H}_3$); 2.74δ (m, 2H, C$\underline{H}_2$CO—); 1.73δ (m, 4H, 2 C$\underline{H}_2$).

| Elementary analysis for C$_{13}$H$_{17}$BrN$_4$O$_3$ | | | | |
|---|---|---|---|---|
| | C | H | Br | N | O |
| Calculated, % | 43.71 | 4.8 | 22.37 | 15.58 | 13.43 |
| Found, % | 43.48 | 4.75 | 22.28 | 15.7 | 13.34 |

(b) N-[2-Keto-6-(3,7-dimethylxanthine-1-yl)hexyl]-4,5,6,7-tetrahydro-thieno[3,2-c]pyridine

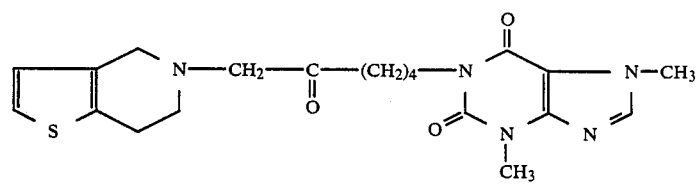

30 Grams (0.084 moles) of 1-(6-bromo-5-keto-hexyl)-3,6-dimethylxanthine and 210 g of acetonitrile were heated to 60° C. in a flask provided with condenser, stirrer and thermometer, in a thermostatized bath. A solution of 11.7 g (0.084 moles) of 4,5,6,7-tetrahydrothieno[3,2-c]pyridine and 9.1 g (0.09 moles) of triethylamine in 80 ml of acetonitrile was quickly added thereto, keeping the inner temperature at 60° C., under stirring. After 4 hours under these conditions, the mixture was cooled at room temperature, then in a refrigerator for some hours. The formed triethylammonium bromide was pump filtered and washed on the filter with acetonitrile (2×20 ml). The filtrate was evaporated under vacuum to dryness, and the residue was freed from the residual triethylammonium bromide by means of 3 extractions in warm with 3×300 ml of $CHCl_3$, which was decanted. The chloroform extracts were filtered, the filtrate was washed with 20 ml of water, then dried over $Na_2SO_4$ and evaporated to dryness under vacuum at 40° C. and 3 mm/Hg. The oily residue (37 g, yield 90% of theoric) showed the following analytical characteristics.

TLC: MeOH/methylene chloride 0.5/9.5, unitary spot, $R_f=0.51$.

$^1$H-NMR ($CDCl_3$) spectrum: 7.51δ (s, 1H,

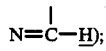

7.05δ (d, 1H, J=4.5 Hz, S—CH=CH); 6.68δ (d, 1H, N=4.5 Hz, S—CH=CH); 4.1δ (superimposed signals, 5H, $CH_3$=$CH_2$); 3.67δ (s, 2H, $CH_2$); 3.57δ (s, 3H, $CH_3$) 3.40δ (s, 2H, $\underline{CH_2}$); 2.87δ (m, 4H, 2 $CH_2$); 2.60δ (m, 2H, —CO—$CH_2$); 1.70δ (m, 4H, 2 $\underline{CH_2}$, CO—$CH_2$—$CH_2$—$CH_2$—$\underline{CH_2}N$).

| Elementary analysis for $C_{20}H_{25}N_5O_3S$ | | | | | |
|---|---|---|---|---|---|
| | C | H | N | O | S |
| Calculated, % | 57.81 | 6.06 | 16.85 | 11.55 | 7.72 |
| Found, % | 57.46 | 6.12 | 16.68 | 11.51 | 7.65. |

From the base, the corresponding bisulfate was obtained by dissolving 40 g (0.096 moles) of the same base, in the warm, at 350 ml of isopropanol/water 90/10 (by volume), and adding a solution of 12.25 g (0.12 moles) of conc. $H_2SO_4$ in 150 ml of isopropanol/water 90/10 (by volume), under stirring. The mixture was warm filtered with 2 g f decolouring coal, thereafter it was cooled first to room temperature, then to 5° C. for some hours. The crystalline precipitate was pump filtered, washed with 2×50 ml of cold isopropanol and dried in oven under vacuum at 70° C. (otherwise, operating under milder conditions, the salt may contain 2 moles of crystallization water). 44.5 Grams of $C_{20}H_{25}N_5O_3S.H_2SO_4$ (LM-PT bisulfate), m.p. 182°-184° C., titre 98-99%.

EXAMPLE 2

(a)

N-(1-Bromo-5-carboxy-pentyl)-4,5,6,7-tetrahydro-thieno[3,2-c]-pyridine

In a 250 ml flask, 18.1 g of 5-bromovalerianic acid (0.1 moles) and 65 g of thionyl chloride (0.55 moles) were placed. 2 Drops of pyridine were added, and the mixture was stirred for 2 hours at a temperature of about 0°-5° C. Stirring was continued overnight at room temperature. The excess thionyl chloride was evaporated off under reduced pressure at 40°-50° C., the residue was treated with 50 ml of anhydrous methylene chloride. 2.8 Grams of 4,5,6,7-tetrahydro-thieno[3,2-c]-pyridine (0.2 moles) dissolved in 50 ml of anhydrous methylene chloride were added dropwise, under stirring, in about 1 hour, at room temperature. Stirring was continued for 3 hours at room temperature, and tetrahydro-thienopyridine hydrochloride precipitated, which was filtered and washed twice with 30 ml of methylene chloride. The organic phases were pooled and washed in turn with 50 ml of a 10% aqueous solution of hydrochloric acid, 50 ml of water, 50 ml of a 5% sodium bicarbonate aqueous solution, finally with 50 ml of water. The solution was dried over anhydrous sodium sulfate, filtered and evaporated under vacuum. 26 grams (87%) of crude compound were obtained, which was directly used in the next step.

(b)

N-[Keto-5-(3,7-dimethylxanthinyl-1-yl)pentyl]-4,5,6,7-tetrahydro-thieno[3,2-c]-pyridine 1.32 Grams (0.044 moles) of a 80% sodium hydride suspension in mineral oil was added to a mixture of theobromine (7.9 g; 0.04 moles) in 200 ml of anhydrous dimethylformamide, under stirring, during about 10 minutes, at a temperature of 70° C. After completion of the addition, temperature was raised to 95°-100° C., and maintained for 3 hours. 12.1 Grams (0.04 moles) of the compound of step (a) were added to the mixture, which was stirred for 20 hours at 95°-100° C. After cooling, the resulting precipitate was filtered and washed with methylene chloride. The pooled organic layers were evaporated at 80°-90° C., the obtained residue was taken up in 150 ml of water and 200 ml of methylene chloride, then treated with a 10% NaOH aqueous solution of pH 13. The two layers were separated, the aqueous phase was extracted with 2×80 ml of methylene chloride, the extracts were combined with the main organic phase, which was washed with 100 ml of water, dried over anhydrous sodium sulfate, filtered and evaporated off. 11 Grams of compound were obtained, which was triturated with diisopropylether, then crystallized from isopropanol, obtaining 8 g (50% yield) of the desired compound, melting at 176°-178° C. A sample of the compound, treated with hot isopropanol, had melting point at 177°-179° C., and the following characteristics:

TLC (thin layer of silica gel; eluent: $CH_2Cl_2$/MeOH, 95:5): unitary spot, $R_f$ 0.55.

$^1$H-NMR ($CDCl_3$) spectrum: 7.42δ (s, 1H, N=C—H); 6.97δ (d, 1H, S—CH=CH); 6.58δ (d, 1H, S—CH=CH); 4.10-3.20δ (superimposed signals, 12H, 2 $CH_3$+3 $CH_2$); 3.00-2.73δ (superimposed signals, 4H, 2 $CH_2$); 2.56δ (t, 2H, —$CH_2$—C=O); 2.7-1.75δ (quintet, 2H, —$CH_2$—$\underline{CH_2}$—$CH_2$—).

| Elementary analysis for $C_{19}H_{23}N_5O_3S$ (M.W. 401.49) | | | |
|---|---|---|---|
| | C | H | N |
| Calculated, % | 56.84 | 5.77 | 17.45 |
| Found, % | 56.65 | 5.79 | 17.46. |

EXAMPLE 3

The same compound of Example 2 may alternatively be obtained starting from 1-(5-carboxymethyl)-pentyl-3,7-dimethylxanthine, obtained by reacting theobromine and methyl 5-bromovalerianate, in the presence of sodium hydride. 1.47 Grams (0.005 moles) of the xanthinic intermediate, 2.07 g (0.015 moles) of 4,5,6,7-tetrahydro-thieno[3,2-c]-pyridine and 0.66 g (0.0025 moles) of rhodium trihydrate chloride were heated at 100° C. for 3 days. After cooling, 15 ml of methylene chloride, then 12.5 ml of a 1N hydrochloric acid solution, were added. The precipitate was filtered and the organic phase was separated, washed with 10 ml of water, dried on anhydrous sodium sulfate, filtered and evaporated off. 2.2 Grams of crude compound were obtained, which was purified by chromatography on silica gel, to obtain 0.78 g of the compound of Example 2, melting at 176°–178° C. and having the same analytical characteristics of the compound of Example 2.

EXAMPLE 4

(a) 1-(2-Keto-5-pentyl)-3,7-dimethylxanthine

A suspension of 80% sodium hydride in mineral oil (3 g; 0.1 moles) was added in small portions during 10 minutes, to a suspension of 18 g (0.1 moles) of theobromine in 400 ml of anhydrous dimethylformamide. The reaction mixture was heated to 95°–100° C. for 3 hours. Then 13.26 g (0.11 moles) of 5-chloro-2-pentanone were added, and the reaction mixture was maintained at 95°–100° C. for 20 hours more. After filtration, the filtrate was evaporated under reduced pressure, the residue was treated with 150 ml of water and the pH was adjusted to 13–14 with a 10% NaOH aqueous solution. The mixture was extracted with 3×80 ml of methylene chloride, the combined organic extracts were washed with 3×50 ml of water, dried over anhydrous sodium sulfate, filtered and evaporated under vacuum. 2.95 Grams (11.2%) of the title compound were obtained, melting at 109°–111° C., which was directly used in the next step. The $^1$H-NMR spectrum was consistent with the formula.

(b) 1-(1-Bromo-2-keto-5-pentyl)-3,7-dimethylxanthine 4.93 Grams (0.031 moles) of bromine were added to a solution of 7.3 g (0.0276 moles) of compound (a) in 100 ml of methanol, at 10° C. After stirring for 15 hours at room temperature, the reaction mixture volume was concentrated to 30 ml under reduced pressure, then 60 ml of water, and 3 drops of conc. sulphuric acid were added. The mixture was stirred at room temperature for 4 hours, in order to hydrolyze any dimethylketals formed by reaction with methanol. After dilution with 50 ml of water, the pH of the mixture was adjusted to 8–9, by addition of a 10% sodium bicarbonate aqueous solution, the mixture was extracted with 3×50 ml of methylene chloride, washed with water, dried on anhydrous sodium sulfate, filtered and evaporated under vacuum. 8.3 Grams of compound were obtained, which, by TLC and NMR analysis, showed to be impure by the presence of the 1-(3-bromo-2-keto-5-pentyl)-3,7-dimethylxanthine regioisomer. The crude compound was directly used for the next step.

(c) N-[2-Keto-5-(3,7-dimethylxanthinyl-1-yl)pentyl]-4,5,6,7-tetrahydro-thieno[3,2-c]-pyridine 2.85 Grams (0.02 moles) of tetrahydro-thieno[3,2-c]-pyridine and a solution of 2.43 g of triethylamine in 30 ml of acetonitrile were added to a solution of the crude product from step (a) in 60 ml of acetonitrile, at 60° C. The mixture was stirred for 6 hours at 65°–70° C., then solvent was evaporated under reduced pressure, the residue was treated with 50 ml of methylene chloride and 50 ml of water and the phases were separated. The aqueous phase was extracted with 2×30 ml of methylene chloride. The combined organic phase were washed with 2×30 ml of water, dried over anhydrous sodium sulfate, filtered and evaporated under reduced pressure. 8.4 Grams of crude compound were obtained, which was purified by chromatography on silica gel, using as the eluent firstly methylene chloride, then methylene chloride:methanol mixtures from 99:1 to 98:2. 4.2 Grams of the title compound were obtained, corresponding to a total yield of 38%.

The obtained compound was pure by TLC analysis and had the following $^1$H-NMR spectrum, which was consistent with the desired structure:

$^1$H-NMR (CDCl$_3$) spectrum: 7.42δ (s, 1H, N=C—H); 6.97δ (d, 1H, S—CH=CH); 4.10–3.20δ (superimposed signals, 12H, 2 CH$_3$+3 CH$_2$); 3.00–2.73δ (superimposed signals, 4H, 2 CH$_2$); 2.56δ (t, 2H, —CH$_2$-C=O—); 2.17–1.75δ (quintet, 2H, —CH$_2$-CH$_2$—CH$_2$—).

(d) Bisulfate salt of compound (c)

Compound from step (c) was dissolved in hot methanol and 1.03 g of 96% conc. sulphuric acid were added dropwise, under stirring, to the solution. The mixture was refluxed for 10 minutes under stirring, and evaporated under reduced pressure. The gummy residue was dissolved at ebollition in 45 ml of an isopropanol/water 9:1 mixture, then it was cooled to room temperature, left to stand for 20 hours and the precipitated compound was filtered, washed with 3×150 ml of isopropanol and dried under vacuum at 75° C., to obtain 3.3 g (65.2%) of the title compound, having softening point at 200° and melting point at 215° C., with decomposition.

The compound showed unitary spot by TLC, and the following analytical characteristics:

Acid-base titre: more than 99%.

| Elementary analysis for C$_{19}$H$_{25}$N$_5$O$_7$S$_2$, M.W. 499.57 | | | |
| --- | --- | --- | --- |
| | C | H | N |
| Calculated, % | 45.68 | 5.04 | 14.02 |
| Found, % | 45.85 | 5.12 | 13.98. |

EXAMPLE 5

(a) 7-(6-Bromo-5-keto-hexyl)-1,3-dimethylxanthine 9.7 Grams (0.06 moles) of bromine were added to a solution of 15 g (0.054 moles) of 7-(5-keto-hexyl)-1,3-dimethylxanthine in 100 ml of anhydrous methanol, at 10° C. with stirring. After 30 minutes at the same temperature, stirring was continued for 7 more hours at room temperature. The mixture was then concentrated under reduced pressure till a residual volume of 30 ml, diluted with 30 ml of water, added with 3 drops of 96% sulphuric acid and stirred for 4 hours at room temperature, to hydrolyze any dimethylketal formed, then diluted with 100 ml of water and alkalized with a 10% sodium bicarbonte aqueous solution. The mixture was extracted with 2×80 ml of methylene chloride, the organic phase was washed with water, dried and evaporated under reduced pressure. The residue was dissolved in 30 ml of ethyl acetate, cooled and crystallized at 5°–10° C. 7.5 Grams (40%) of the title compound were obtained, melting at 106°–109° C., which was directly used in the next step.

(b)
N-[2-Keto-6-(1,3-dimethylxanthine-7-yl)-hexyl]-4,5,6,7-tetrahydro-thieno[3,2-c]-pyridine A solution of 2.78 g of thienopyridine in 20 ml of acetonitrile was added to a solution of 6.9 g of the compound from the previous step in 50 ml of acetonitrile, under stirring, at 60° C. The reaction was continued for 7 hours at 60°–65° C., the solvent was evaporated off and the residue was dissolved in 100 ml of methylene chloride. After dilution with 50 ml of water, the organic phase was separated, washed again with 50 ml of water, dried over anhydrous sodium sulfate, filtered and evaporated under reduced pressure. 7.1 Grams (88.57%) of the title compound were obtained, having the following analytical characteristics:

TLC: (silica gel thyn layer; eluent: MeOH/methylene chloride 0.5:9.5): unitary spot, $R_f$ 0.55.

$^1$H-NMR (CDCl$_3$) spectrum: 7.54$\delta$ (s, 1H, N=C—H); 7.04$\delta$ (d, 1H, S—CH=CH); 6.68$\delta$ (d, 1H, S—CH=CH); 4.29$\delta$ (t, 2H, —N=CH—N—CH$_2$); 3.70–3.30$\delta$ (superimposed signals, 10H, 2 CH$_3$+2 C$\overline{\text{H}}_2$); 3.09–2.80$\delta$ (superimposed signals, 4H, 2 CH$_2$); 2.60$\delta$ (t, 2H, —CH$_2$—C—O); 2.10–1.35$\delta$ (m, 4H, —CH$_2$—C$\underline{\text{H}}_2$—CH$_2$—CH$_2$—).

(c) Bisulfate salt 1.64 grams of 96% sulphuric acid were added to a solution of the compound from step (b), in 50 ml of methanol. An oily precipitate was obtained, which was heated under reflux for 15 minutes. An oily precipitate formed, which solidified by treatment under reflux for 15 minutes. After cooling, the precipitate was filtered and redissolved in 40 ml of hot isopropanol, left to cool for 3 hours at 10° C., filtered again and dried. 5.9 Grams of compound, melting at 178°–180° C., were obtained. After drying under high vacuum at 75° C. for 2 hours, 5.7 g of compound were obtained, softening at about 180° C. and melting at 213° C., having the following analytical characteristics:

Acid-base titre: more than 99%.

$^1$H-NMR spectrum: according to the desired structure.

| Elementary analysis for C$_{20}$H$_{25}$N$_5$O$_3$S.H$_2$SO$_4$, (M.W. 513.6) | | | | |
|---|---|---|---|---|
| C | H | N | O | S |
| Calculated, % 46.77 | 5.30 | 13.63 | 21.81 | 12.49 |
| Found, % 46.25 | 5.99 | 13.63 | 21.84 | 12.55. |

EXAMPLE 6

(a)
N-[2-Keto-5-(1,3-dimethylxanthine-7-yl)pentyl]-4,5,6,7-tetrahydro-thieno[3,2-c]-pyridine The title compound was obtained according to the same procedure of Example 4, replacing theobromine with theophylline. The final compound and its bisulfate salt showed the following characteristics:

$^1$H-NMR (CDCl$_3$) spectrum: 7.54$\delta$ (s, 1H, N=C—H); 7.04$\delta$ (d, 1H, S—CH=CH); 6.68$\delta$ (d, 1H, S—CH=CH); 4.29 (t, 2H, —N=CH—N—CH$_2$); 3.70–3.30$\delta$ (superimposed signals, 10H, 2 CH$_3$+2 C$\overline{\text{H}}_2$); 3.30–2.80$\delta$ (superimposed signals, 4H, 2 CH$_2$); 2.60$\delta$ (t, 2H, —CH$_2$—CO—); 2.10–1.35$\delta$ (m, 4H, CH$_2$—C$\underline{\text{H}}_2$—CH$_2$—).

(b) Bisulfate salt of the final compound: C$_{19}$H$_{25}$N$_5$O$_7$S$_2$: M.W. 499.57

TLC: unitary spot.

M.p.: softening at 194° C.
Melting with dec. at: 216° C.

As already stated, the compounds according to the invention show a marked antiplatelet aggregation activity. Moreover, their toxicity is very low. For example, the acute toxicity of the salt above referred by LM-PT bisulfate, was evaluated in the mouse orally and intravenously. The LD$_{50}$ were about 400 mg/kg and about 100 mg/kg, respectively. The DPPV (disaggregating power percentage value) was evaluated for LM-PT bisulfate, by the ADP induced aggregation test ex vivo in the rat, orally. For a single dose of 100 mg/kg, the DPPV was 92–96%.

The present invention refers also to all of the industrially applicable aspects of compounds of formula I, as agents inhibiting platelet aggregation.

Therefore, a primary object of the present invention comprises pharmaceutical compositions containing compounds I as active ingredients, optionally combined with conventional excipients.

The compounds of the invention may be administered orally, at a daily dose comprised from 1 to 100 mg.

What is claimed is:

1. A compound according to formula (I)

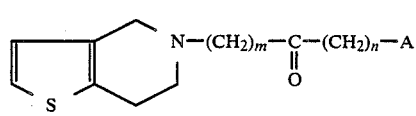

wherein:
m is zero or 1;
n is zero, 1, 2, 3 or 4;
A is 3,7-dimethylxanthine-1-yl or 1,3-dimethylxanthine-7-yl.

2. As a compound according to claim 1, the N-[2-keto-6-(3,7-dimethylxanthine-1-yl)hexyl]-4,5,6,7-tetrahydro-thieno[3,2-c]pyridine.

3. As a compound according to claim 1, the N-[1-keto-5-(3,7-dimethylxanthine-1-yl)pentyl]-4,5,6,7-tetrahydro-thieno[3,2-c]pyridine.

4. As a compound according to claim 1, the N-[2-keto-5-(3,7-dimethylxanthine-1-yl)pentyl]-4,5,6,7-tetrahydro-thieno[3,2-c]pyridine.

5. As a compound according to claim 1, the N-[2-keto-4-(3,7-dimethylxanthine-1-yl)butyl]-4,5,6,7-tetrahydro-thieno[3,2-c]pyridine.

6. As a compound according to claim 1, the N-[2-keto-3-(3,7-dimethylxanthine-1-yl)propyl]-4,5,6,7-tetrahydro-thieno[3,2-c]pyridine.

7. As a compound according to claim 1, the N-[2-keto-6-(1,3-dimethylxanthine-7-yl)hexyl]-4,5,6,7-tetrahydro-thieno[3,2-c]pyridine.

8. As a compound according to claim 1, the N-[1-keto-5-(1,3-dimethylxanthine-7-yl)pentyl]-4,5,6,7-tetrahydro-thieno[3,2-c]pyridine.

9. As a compound according to claim 1, the N-[2-keto-5-(1,3-dimethylxanthine-7-yl)pentyl]-4,5,6,7-tetrahydro-thieno[3,2-c]pyridine.

10. As a compound according to claim 1, the N-[2-keto-4-(1,3-dimethylxanthine-7-yl)butyl]-4,5,6,7-tetrahydro-thieno[3,2-c]pyridine.

11. As a compound according to claim 1, the N-[2-keto-3-(1,3-dimethylxanthine-7-yl)propyl]-4,5,6,7-tetrahydro-thieno[3,2-c]pyridine.

12. A pharmaceutical composition having anti-platlet aggregation activity containing as the principal active ingredient an antiplatlet aggregation effective amount of a compound according to claim 1 together with a pharmaceutically acceptable carrier.

* * * * *